(12) United States Patent
Bourland, III et al.

(10) Patent No.: US 11,701,106 B2
(45) Date of Patent: *Jul. 18, 2023

(54) STEERABLE SUTURE RETRIEVER

(71) Applicant: Composite Surgical, LLC, Coral Gables, FL (US)

(72) Inventors: Charles Rice Bourland, III, Coral Gables, FL (US); John James Valadez, Agua Dulce, CA (US); Sumant Gopal Krishnan, Dallas, TX (US); Joshua Silver Redstone, Dallas, TX (US); Brad Topper, Santa Clarita, CA (US)

(73) Assignee: Composite Surgical, LLC, Coral Gables, FL (US)

( * ) Notice: Subject to any disclaimer, the term of this patent is extended or adjusted under 35 U.S.C. 154(b) by 398 days.

This patent is subject to a terminal disclaimer.

(21) Appl. No.: 16/846,127

(22) Filed: Apr. 10, 2020

(65) Prior Publication Data

US 2020/0360013 A1    Nov. 19, 2020

Related U.S. Application Data

(63) Continuation of application No. 16/533,413, filed on Aug. 6, 2019, now Pat. No. 10,667,805.

(60) Provisional application No. 62/849,568, filed on May 17, 2019.

(51) Int. Cl.
  *A61B 17/04* (2006.01)
  *A61B 17/00* (2006.01)

(52) U.S. Cl.
  CPC .. *A61B 17/0483* (2013.01); *A61B 2017/0042* (2013.01); *A61B 2017/00367* (2013.01); *A61B 2017/00867* (2013.01); *A61B 2017/00946* (2013.01)

(58) Field of Classification Search
  CPC ............ A61B 17/0469; A61B 17/0483; A61B 17/0485; A61B 2017/06009; A61B 2017/00349; A61B 2017/06019
  See application file for complete search history.

(56) References Cited

U.S. PATENT DOCUMENTS

| | | |
|---|---|---|
| 5,439,467 A | 8/1995 | Benderev et al. |
| 5,499,991 A | 3/1996 | Garman et al. |
| 5,755,728 A | 5/1998 | Maki |
| 5,910,148 A | 6/1999 | Reimels et al. |
| 6,074,403 A | 6/2000 | Nord |
| 6,517,552 B1 | 2/2003 | Nord et al. |
| 6,616,674 B2 | 9/2003 | Schmieding |
| 6,620,166 B1 | 9/2003 | Wenstrom et al. |
| 8,679,135 B2 | 3/2014 | Stone et al. |
| 8,808,313 B2 | 8/2014 | Thorne et al. |
| 8,876,840 B2 | 11/2014 | Harada et al. |
| 9,101,356 B1 | 8/2015 | Jordan |
| 9,271,720 B2 | 3/2016 | Stone et al. |
| 9,398,906 B2 | 7/2016 | Stone et al. |
| 9,451,951 B2 | 9/2016 | Sullivan et al. |
| 9,974,537 B2 | 5/2018 | Coughlin et al. |

(Continued)

FOREIGN PATENT DOCUMENTS

| | | |
|---|---|---|
| WO | WO 2020/236531 | 11/2020 |
| WO | WO 2022/183040 | 9/2022 |

*Primary Examiner* — Sarah W Aleman
(74) *Attorney, Agent, or Firm* — Levine Bagade Han LLP

(57) ABSTRACT

A positioning and retrieval device manipulated by carrying element coupled to an handle and driven by an actuator that allows for axial movement and rotational movement of a capturing portion on the carrying element.

22 Claims, 15 Drawing Sheets

(56) References Cited

U.S. PATENT DOCUMENTS

| | | |
|---|---|---|
| 10,667,805 B1 | 6/2020 | Bourland, III et al. |
| 10,973,512 B1 | 4/2021 | Bourland, III et al. |
| 11,154,295 B1 | 10/2021 | Bourland, III et al. |
| 2001/0012945 A1 | 8/2001 | Romano |
| 2003/0015203 A1 | 1/2003 | Makower et al. |
| 2004/0073254 A1 | 4/2004 | Wyman et al. |
| 2004/0087967 A1 | 5/2004 | Schur et al. |
| 2004/0097975 A1 | 5/2004 | Rose |
| 2006/0069399 A1 | 3/2006 | Weisel et al. |
| 2009/0018554 A1 | 1/2009 | Thorne et al. |
| 2010/0114123 A1 | 5/2010 | Nason |
| 2014/0107673 A1 | 4/2014 | Snyder et al. |
| 2014/0128889 A1 | 5/2014 | Sullivan et al. |
| 2014/0188137 A1 | 7/2014 | Spenciner et al. |
| 2014/0222033 A1 | 8/2014 | Foerster et al. |
| 2017/0042533 A1 | 2/2017 | Lunn et al. |
| 2017/0325806 A1 | 11/2017 | Adams et al. |
| 2017/0347997 A1 | 12/2017 | Breslich |
| 2018/0116652 A1 | 5/2018 | Torrie |
| 2019/0290301 A1 | 9/2019 | Prior et al. |
| 2021/0353282 A1 | 11/2021 | Bourland, III et al. |
| 2021/0378662 A1 | 12/2021 | Bourland, III et al. |

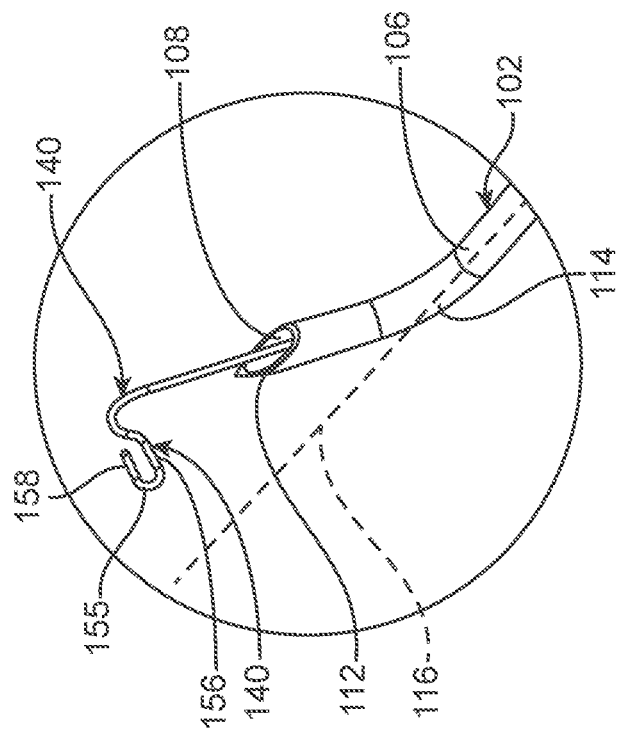
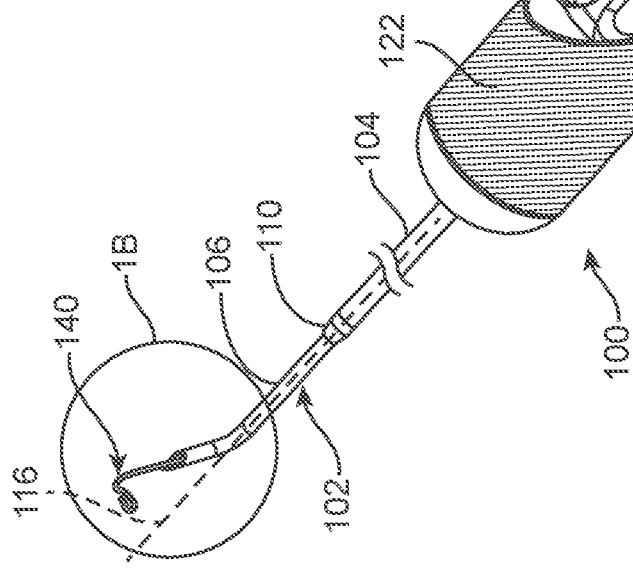

STEERABLE SUTURE RETRIEVER

CROSS-REFERENCE TO RELATED APPLICATIONS

This application is a continuation of U.S. patent application Ser. No. 16/533,413 filed Aug. 6, 2019, which is a non-provisional of U.S. Provisional application 62/849,568 filed on May 17, 2019, the entirety of each of which is incorporated by reference.

BACKGROUND OF THE INVENTION

Suturing techniques and instruments facilitate the suturing of tissue during endoscopic and open surgical procedures. The term "endoscopic" encompasses arthroscopy, laparoscopy, hysteroscopy, etc., and endoscopic surgery involves surgical procedures that are performed on a patient's through small openings as opposed to conventional open surgery through large incisions. The access to a surgical site in an endoscopic procedure relies on one or more portals created in the patient's body or through one or more cannulas inserted into the patient's body through small incisions. The use of sutures in endoscopic procedures relies on remote retrieval of the suture when it is passed through, tied to, and/or anchored in tissue of the surgical site.

Various instruments and techniques exist and are used for surgical repairs requiring the passing of sutures back through tissue. For example, a suture snare is used with suture passers to retrieve the suture within the joint space during endoscopic surgery. Due to the limited space within the joint, deployment of the snare is often challenging. There remains a need for a minimally invasive surgical instrument that can retrieve or pass a suture or similar surgical item, where the device can allow for steerability as well ease of manipulation to grasp or release a suture used in a surgical procedure.

BRIEF SUMMARY OF THE INVENTION

The illustrations and variations described herein are meant to provide examples of the methods and devices of the invention. It is contemplated that combinations of aspects of specific embodiments or combinations of the specific embodiments themselves are within the scope of this disclosure.

The present disclosure includes a surgical instrument for manipulating a component within a patient. The devices and methods described herein can manipulate by positioning or retrieving the component. Such components include, but are not limited to, sutures, anchors, clips, staples, or any surgical component used in a medical procedure. The devices and method described herein can be used in any open surgical procedure or any procedure performed via arthroscopic, endoscopic, thorascopic or similar means.

In one example, an instrument according to the present disclosure includes a shaft having a far portion, a near portion, and an arcuate shaft segment located between the far portion and the near portion such that a far end of the shaft extends radially away from an axis of the near portion; a lumen extending through the shaft and exiting at the far portion; a handle fixed relative to the near portion of the shaft, such that rotation of the handle causes rotation of the shaft; a suture carrying element comprising a main segment, a capture portion at a distal end, and an arcuate element segment proximal between the capture portion and the main segment, such that in an unconstrained configuration the capturing portion extends radially away from an axis of the main segment, the suture carrying element being elastically deformable into a constrained configuration when located within the lumen; and an actuator housed in the handle and coupled to the main segment of the suture carrying element, the actuator being moveable relative to an axis of the handle simultaneously in a rotational direction and in an axial direction, such that the suture carrying element can be simultaneously rotated and advanced relative to the shaft using the actuator.

In one variation of the surgical instrument of claim 1, the arcuate segment is configured such that when moved with the opening at the far portion the arcuate segment deflects to cause the capturing portion to move through an arc such that rotation of the suture carrying element can reposition the capturing portion within an increased distance without moving the far portion of the shaft. The arcuate segment can also be configured to cause the capturing portion to re-enter the opening at the far portion in a single position relative to the opening.

In another variation, the actuator is positioned within the handle and is moveable relative to the axis of the handle simultaneously in the rotational direction and in the axial direction while the handle remains stationary.

A variation of the instrument can further include a torque shaft extending in the lumen and coupling the main segment to the actuator, wherein a torsional stiffness of the torque shaft is greater than a torsional stiffness of the main segment such that the torque shaft transfers rotation to the main segment.

In one variation the torque shaft comprises a stainless steel hypodermic tubing. Alternatively, or in combination, the torque shaft can comprise a reinforcement member coupled to a portion of the main segment to form a reinforced segment, such a torsional stiffness of the reinforced segment is greater than a torsional stiffness of a remainder of the main segment such that the torque shaft transfers rotation to the remainder of the main segment.

Variations of the device include a capturing portion that extends in a u-shaped profile having a first leg and a second leg with an opening therebetween, the first leg being continuous with the arcuate element segment.

In an additional variation, an arc of the arcuate element segment is greater than 90 degrees such an apex of the arcuate element segment is positioned distally of the first leg, such that when a suture is located against the apex, distal movement of the suture capturing element urges the suture into the u-shaped profile.

Variations of the surgical instrument include a shaft that is rigid or malleable. Alternate variations include a rigid shaft with a malleable section.

Variations of the instrument include a capture portion that comprises a u-shape having a first leg connected to the arcuate element segment, a second leg having a free end and a u-segment between the first leg and the second leg, where the u-segment forms a seat for the suture. In additional variations, the capture portion is angled 45 degrees relative to an axis of the main segment.

Surgical instruments of the present disclosure can optionally include a sharp tip located at the distal end which allows the distal end of the rigid shaft to penetrate through soft tissue when advanced therethrough.

In variations of the device, the handle of the instrument further comprises a window opening and where the actuator is accessible through the window opening. In certain variations, the actuator is recessed within the window opening.

The suture carrying element can comprise a superelastic alloy. The capture portion can include an opening disposed proximal to the distal end including a distal concave surface facing proximally for retaining the suture within the opening as the instrument is drawn proximally. In some variations, the capture portion comprises a pivotably operable jaw. Alternatively, the capture portion comprises a v-shape having an apex and an open end, where the apex is distal to the open end.

The present disclosure also includes methods for manipulating a suture passed through a tissue region. For example, one such method includes positioning a shaft adjacent to the tissue region using a handle, where the shaft is affixed to the handle such that rotation and axial movement of the handle produces rotation and axial movement of the shaft, the shaft having an arcuate segment proximate to a sharp distal tip; passing a distal opening of the shaft through the tissue region and advancing the shaft through the tissue region using the handle; manipulating an actuator in the handle to advance a suture carrying element through a lumen of the shaft, where the suture carrying element a main segment, a capture portion at a distal end, and an arcuate element segment proximal between the capture portion and the main segment, such that in an unconstrained configuration the capturing portion extends radially away from an axis of the main segment, the suture carrying element being elastically deformable into a constrained configuration when located within the lumen; simultaneously rotating the handle while rotating and axially moving the actuator to engage the suture with the capturing portion; proximally moving the actuator relative to the handle to retract the capturing portion and the suture within the shaft; and retrieving the shaft through the tissue region to pull the suture through the tissue region.

In one variation of the method, proximally moving the actuator relative to the handle to retract the capturing portion and the suture within the shaft causes the arcuate element segment to deform when withdrawn into the distal opening of the shaft causing the capturing portion to move towards an axis of the distal end of the shaft without deforming the capturing portion.

The present disclosure also includes a medical device comprising: a handle portion having a cylindrical bore; an actuator having a cylindrical periphery that forms a slidable fit with the cylindrical bore; a shaft fixed relative to the handle portion; a torque shaft fixed to the actuator, where rotation and/or axial movement of the actuator causes rotational and/or axial movement of the torque shaft; a fixed component secured to a distal end of the shaft; and an actuatable component coupled to both the fixed component and the torque shaft, where movement of the actuator causes movement of the actuatable component relative to the fixed component.

DESCRIPTION OF THE DRAWINGS

Each of the following figures diagrammatically illustrates aspects of the invention. Variation of the invention from the aspects shown in the figures is contemplated.

FIG. 1A illustrates a variation of a surgical instrument for manipulating or retrieving an item such as a suture.

FIG. 1B illustrates a magnified view of the section 1B from FIG. 1A.

DETAILED DESCRIPTION

Figure 2A:
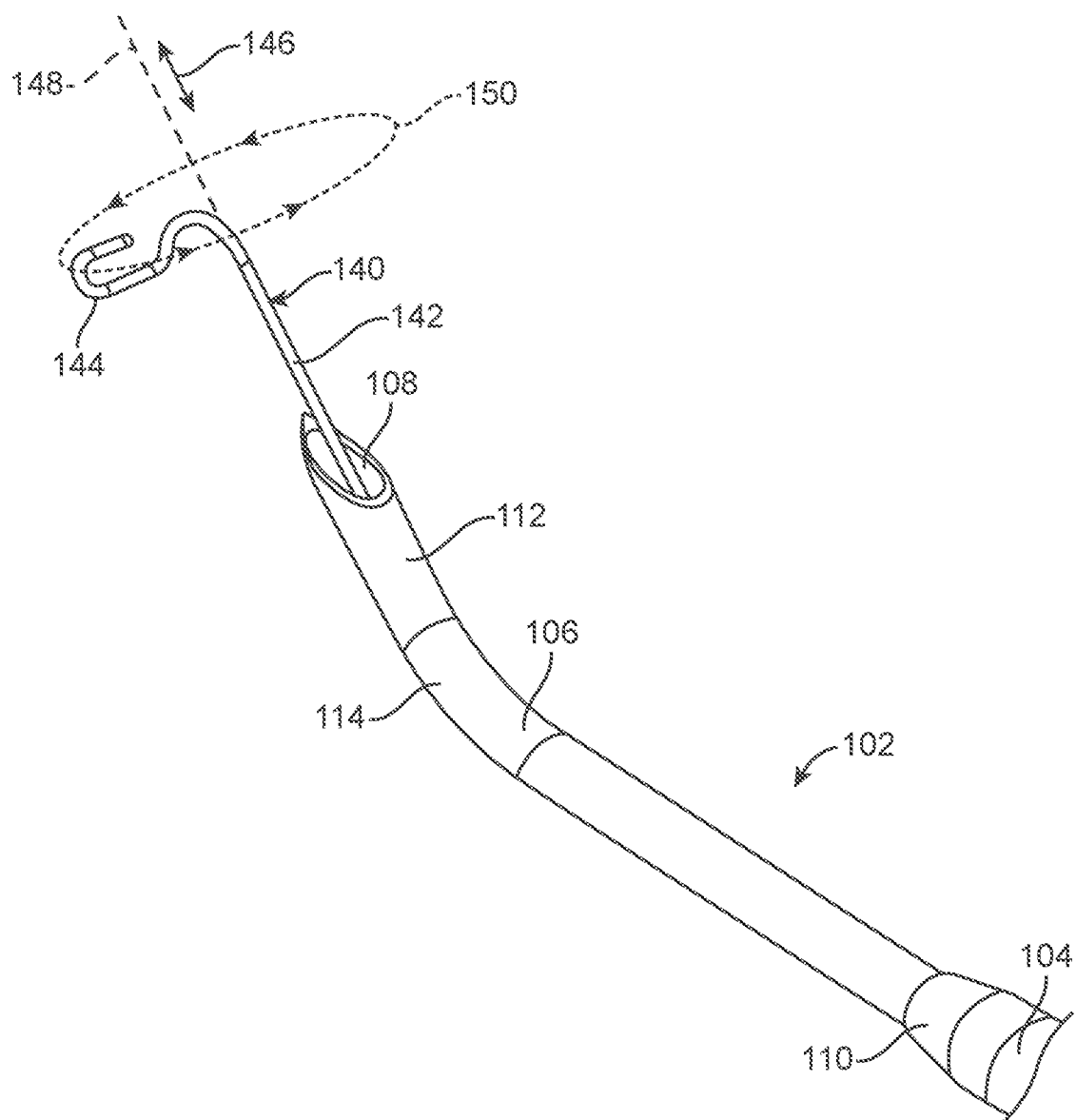
FIG. 2A illustrates another magnified view of a shaft of an instrument to better illustrate movement of a carrying element within a lumen of the shaft.

It is understood that the examples below discuss uses in minimally invasive arthroscopic procedures. However, unless specifically noted, variations of the device and method are not limited to use in arthroscopic procedures. Instead, the invention may have applicability in various parts of the body under any minimally invasive or invasive procedure. Moreover, the invention may be used in any procedure where the benefits of the method and/or device are desired.

FIG. 1A illustrates a variation of a surgical instrument 100 for manipulating an item (not shown in FIG. 1A) during a medical procedure. For the sake of illustration, the item being manipulated is depicted as a suture and one variation of the surgical instrument comprises a suture retriever/manipulator. However, variations of the surgical instrument are not limited to sutures. For example, the instrument can be used to manipulate or retrieve implants, fabric (such as gauze or sheets), threads, wires, etc. As shown in FIG. 1A, a variation of the instrument 100 includes a shaft 102 coupled to a handle 120. The shaft 120 can include a near portion 104 (e.g., a section of the shaft 102 that is adjacent the handle 120) and a far portion 106 (e.g., a section of the shaft 102 that is towards a distal end 108 of the shaft 102). In the illustrated variation of the instrument 100, the far portion 106 includes an arcuate or angled segment 114 that causes a far end 112 of the shaft 102 to extend at an angle or radially away from an axis 116 of the shaft 102. Variations of devices described herein can include shafts 102 with angled segments 114 that produce an angle greater than 0 degrees to 90 degrees. However, the disclosure includes any angle as well as straight shafts. Moreover, in alternate variations the angled segment 114 can also be located at the near portion 104 of the shaft 102.

The medical apparatus 100 illustrated in FIG. 1A also shows a near portion 104 separated from a far portion 106 by a tapered transition section 110. Alternative variations of the device do not require the different sections of the shaft 102 to be different diameters or different configurations. However, varying diameters of the shaft 102 can provide benefits depending upon the main intended procedure of the device. For example, in the variation illustrated in FIG. 1A, a shaft 102 with a larger diameter at the near portion 104 provided for increased column strength when manipulating the instrument 100 via the handle 120. The smaller diameter far portion 106 of the shaft 102 reduces a force required to advance through tissue. In alternate variations, a device 100 according to the present disclosure includes various portions (e.g., 104, 106) having different cross-sectional profiles than the circular profiles shown.

FIG. 1B illustrates a magnified view of the section 1B from FIG. 1A. FIG. 1B shows a lumen 108 that extends through the shaft 102, exiting at the far end 112. Variations of the device 102 can include a shaft lumen 102 that extends into the handle 120. In alternate variations of the device, the lumen can exit from other portions of the shaft not just the far end 112. Moreover, alternate variations of the device 100 include one or more lumens that exit through multiple portions of the device and/or shaft. In any case, the shaft 102 can include a main lumen 108 that accommodates a carrying element 140, which as described below, can be advanced, retracted, and/or rotated using controls coupled to the handle 120. The carrying element 140 is referred to herein as a suture carrying element 140, however, the carrying element 140 can be used to manipulate and/or retrieve a number of surgical items as described above. FIG. 1B also illustrates the far end 112 as having a sharp tip that can penetrate tissue. Alternate variations of the instrument 100 do not require a sharp tip. Instead, the tip can be rounded or blunted to dissect tissue.

FIG. 1B also illustrates a variation of a capture portion 144 being configured in a U-shape with a first leg 156 adjacent to the arcuate segment 152 of the carrying element 140 and a second leg 158 being open to permit positioning of a suture (or other component) adjacent to a seat 155 of the capturing portion. As noted herein, and shown below, the devices described herein can include capturing portions of various shapes as well as actuatable arms or graspers.

FIG. 1A also shows a handle 120 located adjacent to the near section 104 of the shaft 102. Variations of the instrument 100 include handles 120 that are affixed to or relative to the shaft 102 such that rotation of the handle 120 causes rotation of the shaft 102. The handle 120 also includes an actuator 130 that is coupled to the carrying element 140 and allows for movement of the carrying element 140 relative to the shaft 102. In the illustrated variation, as also discussed below, the actuator 120 can allow for rotational and/or axial movement of the carrying element 140 relative to the shaft. In this variation of the instrument 100, the handle 120 includes a body 120 with a window 124 that exposes the actuator 130. This configuration allows for rotation of the handle 120 without any features of the actuator 130 that protrude from the handle body 122. In alternate variations, a portion of the actuator 130 can protrude from the handle body 122. The actuator 130 can include features, such as the recessed pockets 132, that ease positioning of an operators fingers while the operator's hand is able to grasp the remaining portion of the handle body 122. This allows control of the handle 120 and simultaneous adjustment of the actuator 130 using a single hand. Although not illustrated, the recessed features 132 of the actuator can extend around a circumference of the actuator 130.

FIG. 1A further shows an optional feature of the handle 120 where a proximal opening 126 for a lumen that is in fluid communication with the shaft lumen 108. This allows for flushing of the shaft 102 or advancement of a suture through the device.

FIG. 2A illustrates another magnified view of a shaft 102 of an instrument to better illustrate movement of the carrying element 140 within the lumen 108 of the shaft 102. The capturing element 142 can comprise a main segment 142 that is elastically deformable such that it can navigate any bend or arcuate segment 114 of the shaft 102 without retaining the deformation. In certain variations, the main segment 142 and/or entire capturing element 140 is fabricated from a super elastic alloy or a flexible material (e.g., alloy, polymer, or similar material). The carrying element 140 is coupled to the actuator (not shown) along a portion of a proximal end of the main segment 142, wherein rotation of the actuator causes the capturing element 140 to rotate. Furthermore, axial movement of the actuator (or other component) along an axis of the handle (not shown) will cause axial movement 146 of the capturing element 140 about an axis 148 of the main segment 142. Rotation of the actuator also causes the capturing element 140 to rotate about the axis 148 causing a capture portion 144 to rotate in a pattern up to a 360 degree pattern 150.

Figure 2B:
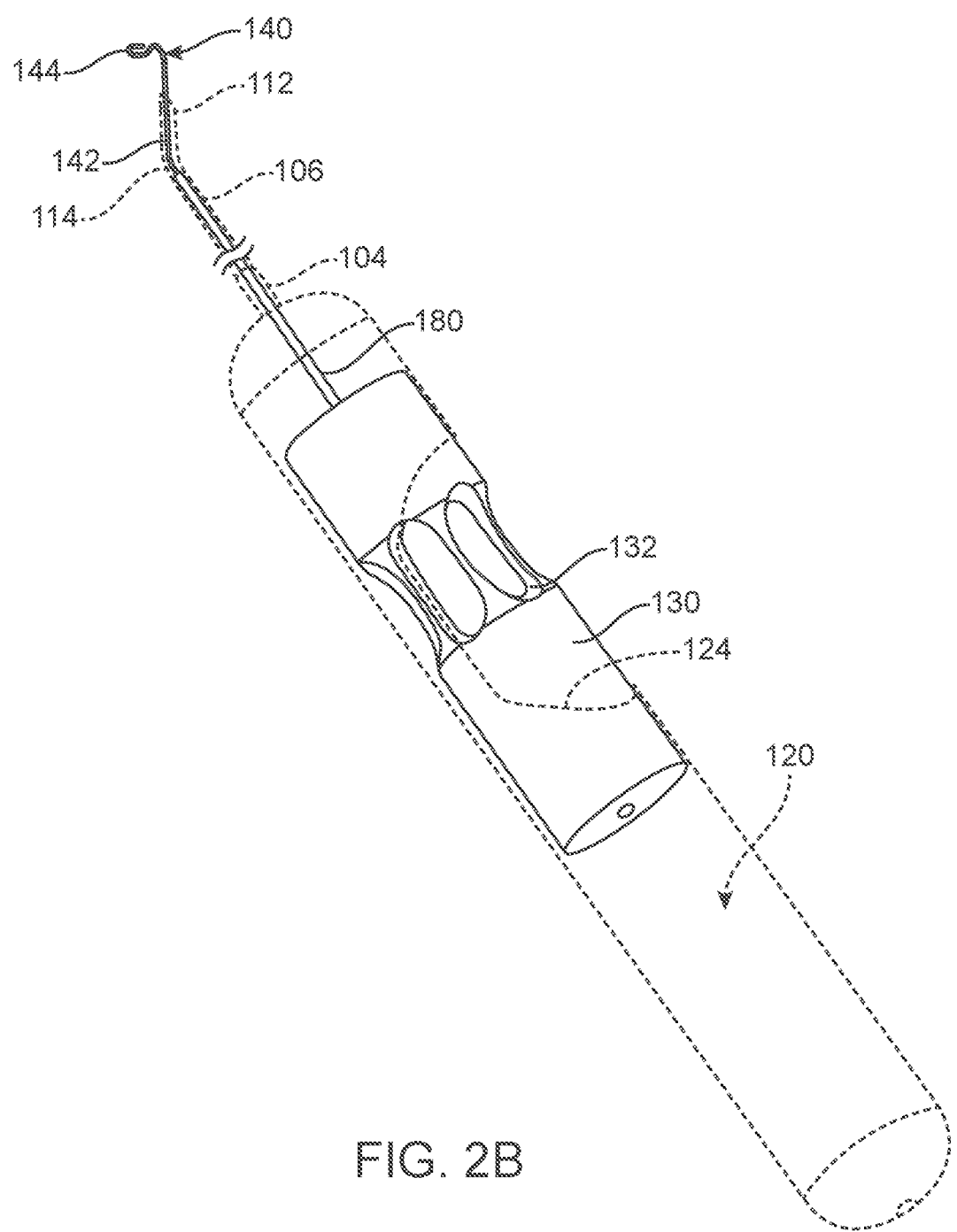
FIGS. 2B and 2C illustrate a device with a torque shaft or reinforced carrying element.

FIG. 2B illustrates an actuator 130 coupled to a carrying element 140 via a torque shaft 180. The torque shaft 180 provides a connection between the carrying element 140 and actuator 130 but also provides a torsional strength or stiffness that allows the actuator 130 to transfer a consistent rotation to the carrying element 140 in addition to providing an axial translation (in those variations requiring both rotation and axial movement). In those previous devices without a torque shaft the wire used to secure the suture twists and binds if over-rotated. The torque shaft 180 of the present disclosure can extend the distance of the shaft 102 with the carrying element 140 connected to a distal end of the torque shaft 180. The torque shaft 180 can also provide provides rigidity and linear structure to the device. In alternate variations, a carrying element 140 can be directly coupled to the actuator 130 but forms a torque shaft 180 using a reinforcement member (e.g., sheath, coating, tube, etc.) over a portion of the main segment 142 of the carrying element 140. In such a case, similar to the torque shaft, the reinforcement allows the actuator 130 to transfer rotation to the capture portion 144 while minimizing binding and torque/torsion loading of the capture portion 144.

Figure 2C:
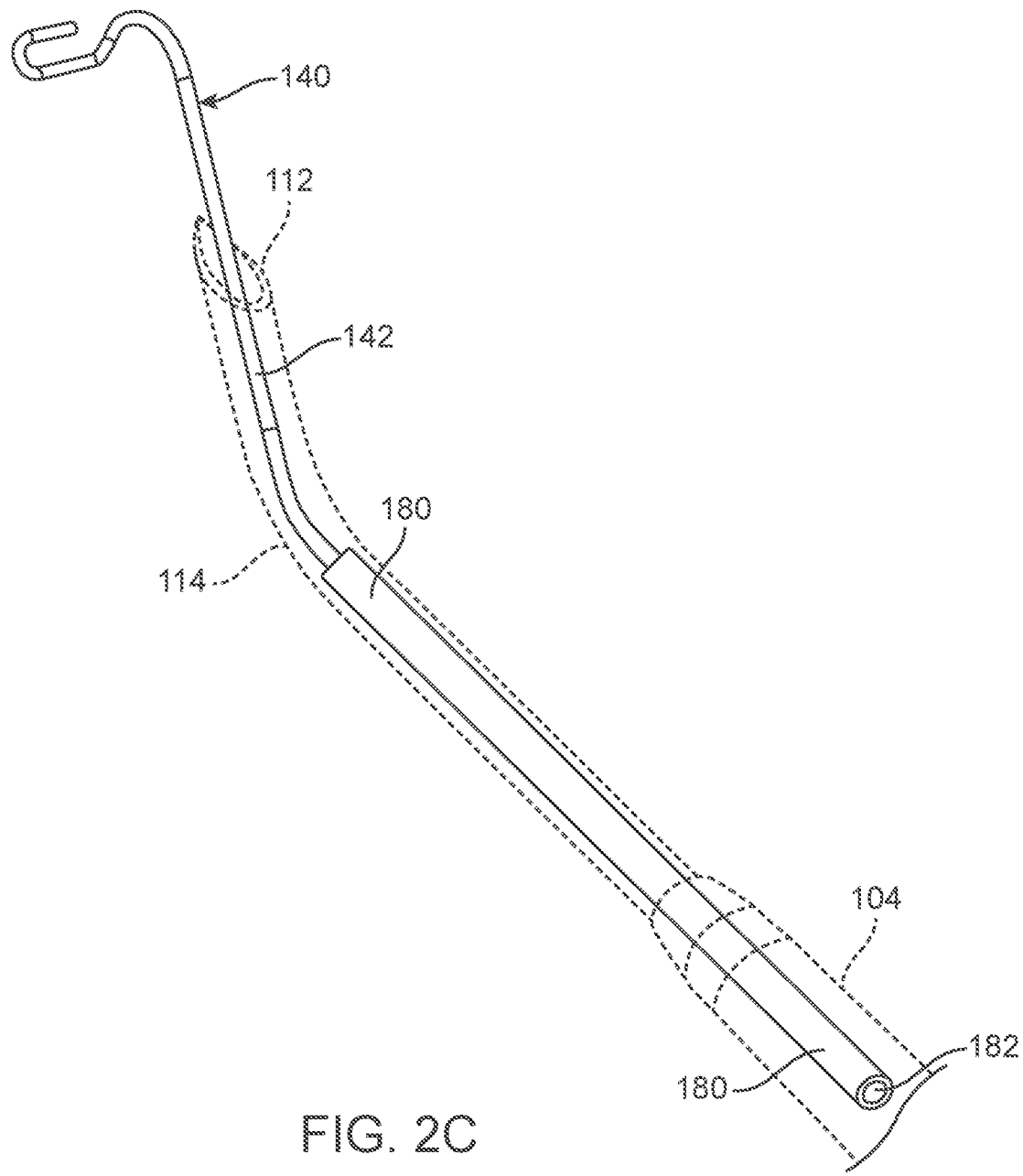

FIG. 2C illustrates a magnified view of a variation of a carrying element 140 and torsion shaft 180. As illustrated, the torsion shaft 180 can comprise a hypotube (e.g., stainless steel) that includes a passage 180, where the main segment 142 is loaded within the passage 180 at a distal end of the torsion shaft 180. Variations of the device can include a torsion shaft 180 (or reinforcement) that does not enter the articulated segment 114 of the shaft. Alternatively, the torsion shaft 180 (or reinforcement) can extend at least partially into or beyond the articulated segment 114.

FIGS. 3A to 3H illustrate an example of a carrying element 140 extending distally from a lumen or opening 108 in a distal end 112 of a shaft 102 of an instrument as described herein. As noted above, a main segment 142 of the carrying element 140 can be axially advanced in a direction 146 relative to the shaft 102. In variations of the device 100, the carrying element 140 can be positioned entirely within the shaft 102 and advanced distally from the opening 108 as needed. The carrying element 140 includes a capturing portion 144 that is typically at a distal end. In the illustrated variation shown in FIG. 3A, the capturing portion 144 extends away from an axis 148 of the main segment 142. As discussed below, providing the capturing portion 144 at a distance from the axis 148 of the main segment increases the ability of an operator to reposition the carrying element 140 and capture section 144 through a range of positions adjacent to the distal end 112 of the shaft 102. In the illustrated variation of FIG. 3A, the capturing portion 144 is positioned approximately 90 degrees from the axis 148 of the main segment 142. However, variations of devices can include a capturing element with an angular spacing that ranges between 0 and 180 degrees relative to the axis 148 to extend in a radial direction from the axis 148 of the main segment. For convenience, the angle can be measured from either leg of the capture portion 144. In order to position the capture portion 144 at an angle to the main segment axis 148, the carrying element 140 can include one or more arcuate sections/segments 152 between the capturing portion 144 and the main segment 142.

Figure 3A:
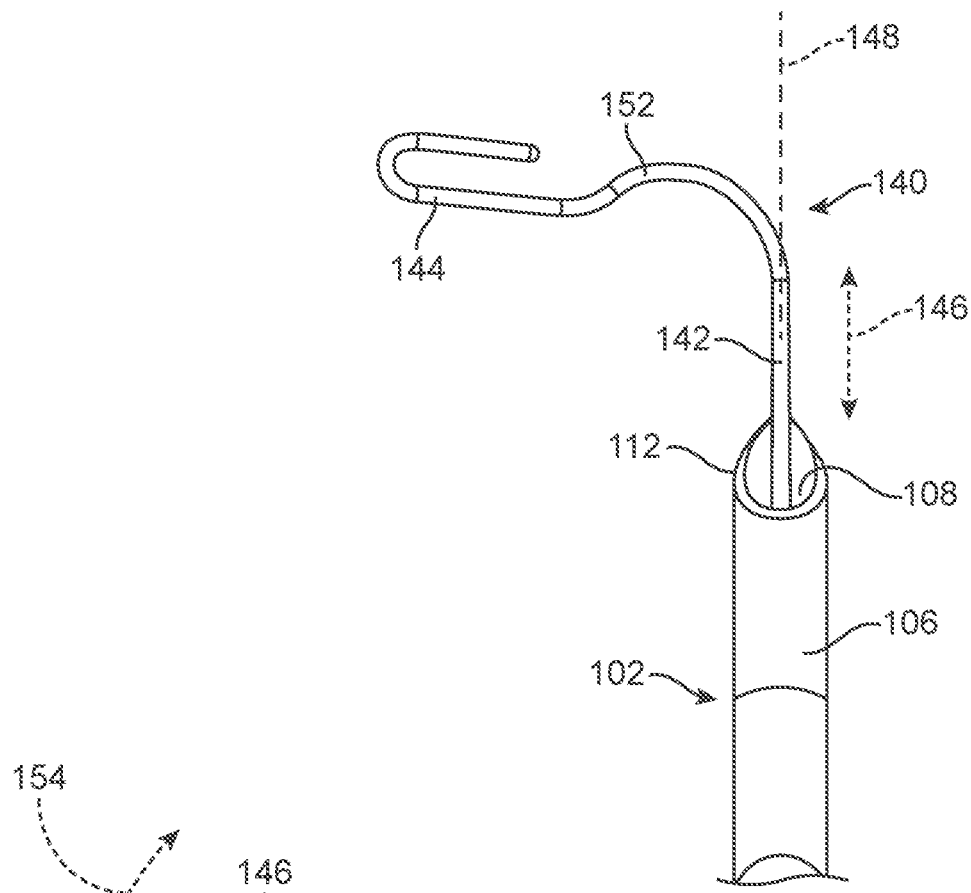
FIGS. 3A to 3H illustrate examples of carrying elements extending distally from a lumen or opening in a distal of a shaft of an instrument as described herein.
Figure 3B:
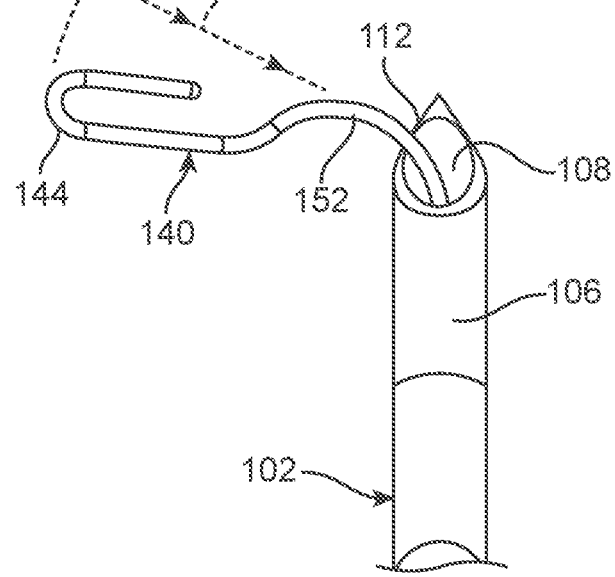

FIG. 3B illustrates a configuration where the carrying element 144 has been withdrawn proximally towards the shaft 102 such that the main segment (not pictured) is within the shaft 102 and the arcuate segment 152 engages a side of the distal end 112. Continued withdrawal of the carrying element 140 in the proximal direction 146 will cause the capturing portion 144 to move in an arc 154 and into alignment with the lumen 108 of the shaft 102. Movement of the capturing portion 144 in an arc pattern 154 is desirable to prevent the suture (or other item being carried) from engaging a side of the wall of the distal end 112. This arc pattern 154 movement is primarily made possible by the large radiused arcuate segment 152.

Figure 3C:
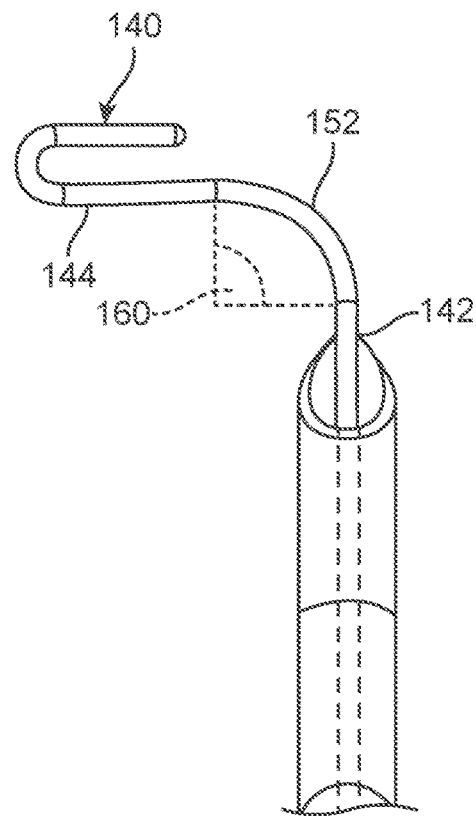
Figure 3D:
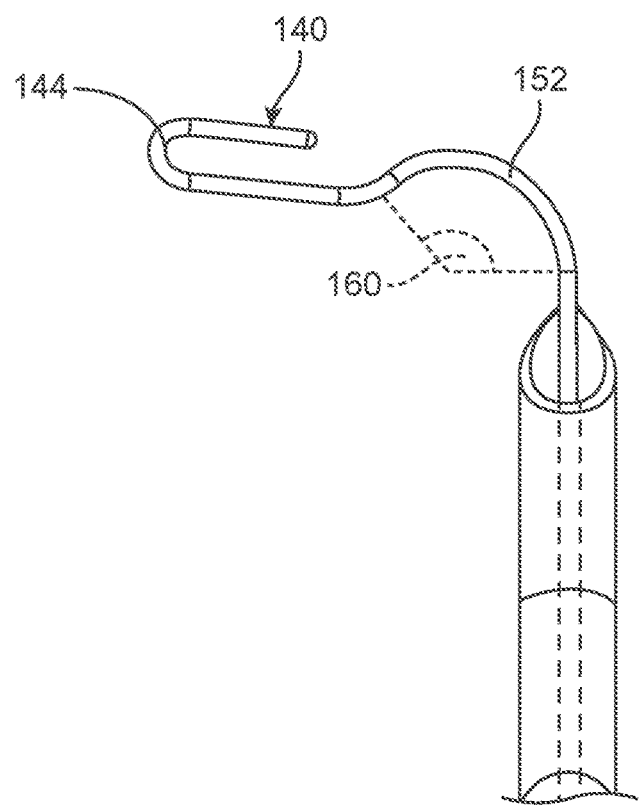

FIGS. 3C and 3D illustrate additional variations of the capturing element 140 to illustrate the features of an arc angle of the arcuate segment 152 of the capturing element 140. The arc angle can be measured starting from the location where the arcuate segment 152 deviates from an axis of the main segment 142 to location where the arcuate segment 152 becomes parallel to or meets a leg of the capturing portion 144. In FIG. 3C, the sweep angle 160 of the arcuate segment 152 is approximately 90 degrees. In FIG. 3D, the arc angle 160 is greater than 90 degrees. It is believed that an arc angle greater than 90 degrees coupled with a large radius arc segment 152 improves the ability of the device to retrieve a suture or similar structure within an opening of the shaft. The combination of arc angle and large radius arc segment (coupled with the repositioning of the shaft) provides an increased range for an operator to maneuver the carrying element from the location where it passes through tissue to a location where a suture (or other medical item) is located.

Figure 3E:
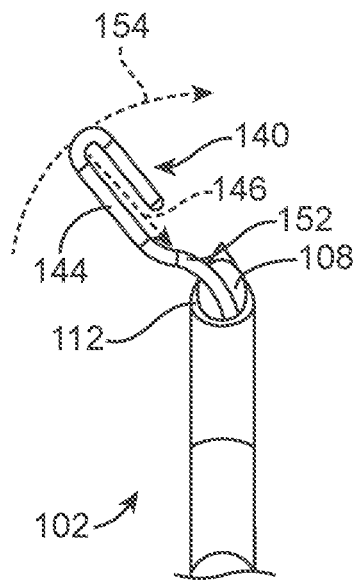
Figure 3F:
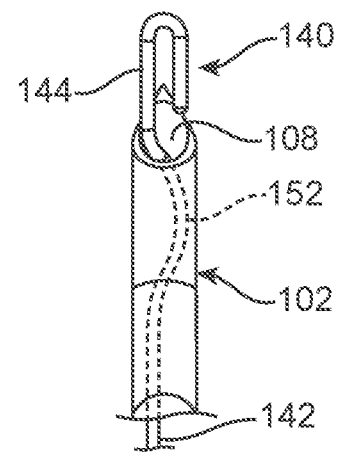
Figure 3G:
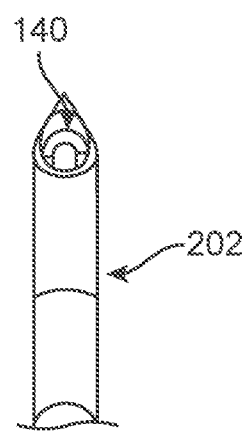
Figure 3H:
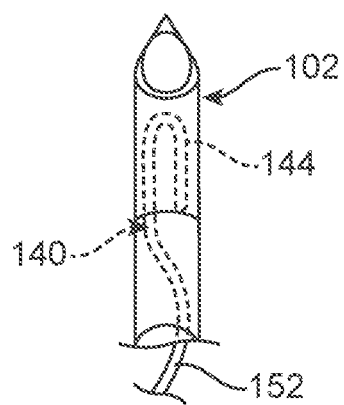

FIG. 3E illustrates a variation of the carrying element 140 that includes an arc angle greater than 90 degrees where the carrying element 140 is retracted in a proximal direction 146 to within the shaft 102. As shown, the capturing portion 144 continues to move in an arc 154 (relative to FIG. 3B) as the arcuate segment 152 engages a wall of the distal end 112 when withdrawn into the shaft 102. FIG. 3F illustrates a state of the instrument when the arcuate segment 152 is within the shaft 102. As shown, because the arc angle is greater than 90 degrees, the capture portion 144 can enter the shaft in alignment with the opening/lumen 108. FIG. 3G shows the carrying element 140 as it retracts into the shaft until the carrying element 140 and capture portion 144 are fully within the shaft 102. As shown, retracting the carrying element 140 causes the arcuate element segment 152 to deform against the distal end such that the capturing portion 144 sweeps to move towards alignment with an axis of the opening 108 (as shown in FIGS. 3F and 3G) without deforming during movement outside of the shaft 102. In certain variations, the capturing portion 144 (either entirely or a portion thereof) can deform as it enters the shaft lumen 108, which compresses the suture (or component). This configuration allows for a suture to be retained within or against the capturing portion 144 as it is repositioned outside of the shaft and prepared for withdrawal into the shaft.

It should be noted that variations of the instruments described herein include the ability to retract the carrying element 140 (as shown in FIGS. 3A to 3B and 3D to 3H) while simultaneously rotating (as demonstrated in FIG. 2A). The ability to move axially while simultaneously rotating allows for increased positioning of the capturing portion 144 during positioning of the carrying element 140 when trying to secure the suture (or other medical component) as well as allows for the capture portion 144 to be rotated when a suture (or other medical component) is secured therein. In the latter case, rotation of a suture (or other element) secured within the capture portion 144 can cause the suture to wrap about the carrying element 140, which further assists in manipulation of the suture.

Another feature of the present device is that the distal end 112 of the shaft 102 comprises a tapered or beveled end at the opening 108. In such variations, the tapered opening 108 as well as the shape and angle of the arcuate segment 108 of the carrying element 140 allows the capture portion 144 to slightly deform such that it enters the opening 108 in a consistent manner regardless of the position of the carrying capture portion 144 when extended. As noted above, variations of the device rely on a torque shaft that is connected to the actuator. Therefore, the relatively short length of the capture portion 144 and main segment that is not reinforced allows the main segment to flex as it re-enters the shaft 108.

In variations of the device, the arcuate segment provides an advantage in being configured such that when moved with the opening at the far portion the arcuate segment 152 deflects to cause movement of the capturing portion 144 through an arc 154. This allows the capturing portion to move through a range of positions such that rotation of the suture carrying element can reposition the capturing portion within an increased distance to reach a suture without having to move the far portion of the shaft. Another benefit is that in variations of the device, the arcuate segment is configured to cause the capturing portion to re-enter the opening at the far portion in a single position relative to the opening. This means that regardless of the orientation of the capturing portion 144 (e.g., if it is rotated 180 degrees from that shown in FIG. 3E, the capturing portion will orient as shown in FIGS. 3E and 3F when retracted within the shaft 102.

Figure 4:
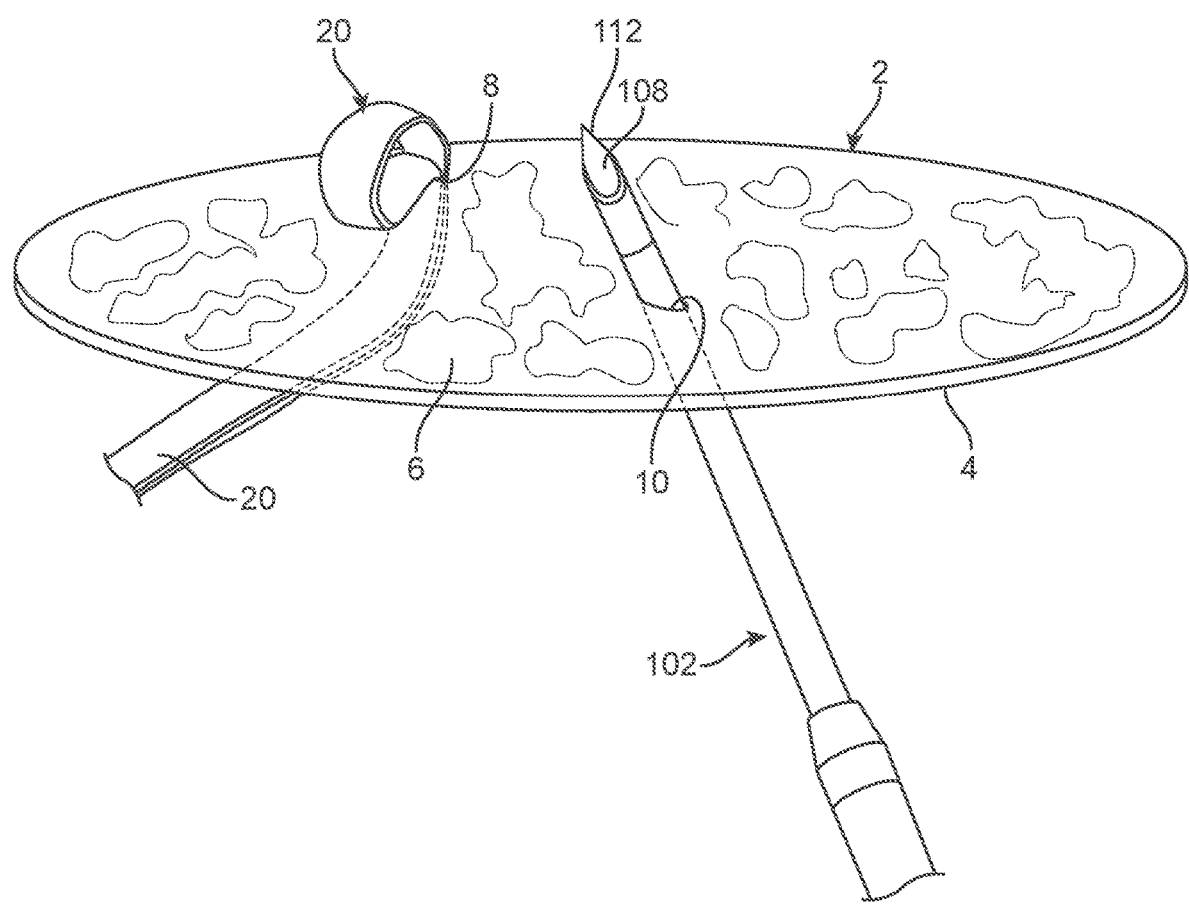
FIG. 4 provides an illustrated example of positioning a shaft of an instrument through tissue.

FIG. 4 provides an illustrated example of positioning a shaft 102 of an instrument according to the present disclosure. For purposes of illustration FIG. 4 shows a section of tissue 2 having a first surface 4 and a second surface 6. The instruments described herein are especially useful in applications where a suture 20 extends from a first surface 4 to a second surface 6 through an opening 8 and must be withdrawn back through the tissue 2 from the second surface 6. In some cases, the medical practitioner only has visual access to the second surface 6 while manipulating the instrument from the first surface 4. FIG. 4 illustrates the suture 20 as having a loop configuration. However, other configurations (e.g., a knot, hook, attached needle, etc.) are considered to be within the scope of this disclosure. Furthermore, the illustrated suture 20 is shown to be a ribbon type configuration. However, the present disclosure includes sutures (or other medical components) of multiple shapes, sizes, and cross sections.

FIG. 4 illustrates a situation where a medical practitioner advances the shaft 102 through an opening 10 in the tissue 2 where the shaft 102 includes a distal end 112 with a sharp tip. However, alternate variations of the device include blunted, atraumatic, or otherwise rounded ends. In the initial advancement of the shaft 102, the opening 108 might be mis-aligned with the suture 20.

Figure 5A:
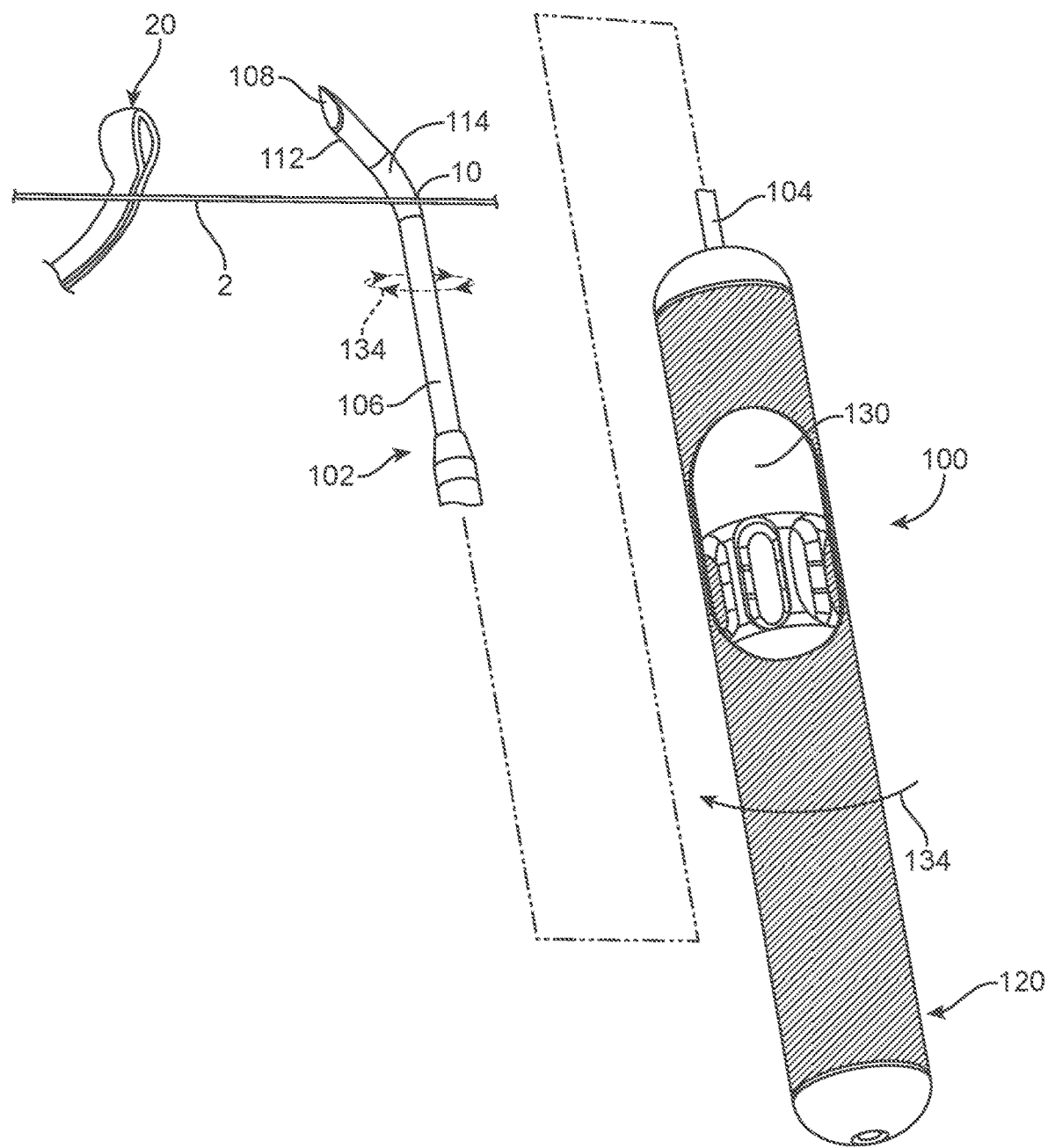
FIGS. 5A to 5F illustrate an example of manipulating a variation of a surgical instrument of the present disclosure to secure a suture 20.

FIGS. 5A to 5F illustrate an example of manipulating a variation of a surgical instrument 100 of the present disclosure to secure a suture 20. As noted herein, the devices disclosed herein can position, retrieve, or otherwise manipulate a suture or other surgical component. FIG. 5A illustrates a state immediately after the shaft 102 is advanced through tissue 2. For purposes of illustration, the shaft 102 and handle 120 are not drawn to scale.

As shown in FIG. 5A, once the shaft 102 of the device 100 is positioned through tissue 2, the handle 120 can be rotated in either direction 134 to produce a corresponding rotation 134 of the shaft 102. In most cases, the medical practitioner will be able to manipulate the handle 120 while visually observing the distal end 112 of the shaft 102. In alternate variations, the shaft 102 can be made sufficiently radiopaque (or have radiopaque markers) such that it is observable under x-ray or a CT scan. Alternatively, the device can be made to be visible under alternate non-invasive imaging (e.g., visible under ultrasound imaging, etc.). Regardless, the medical practitioner can position the far/distal end 112 of the shaft 102 such that the opening/lumen 108 is placed sufficiently close to the suture 20. The arcuate segment 114 of the shaft 102 can further increase the ability to position the opening 108 of the shaft 102 away from the tissue opening 10 by axial movement of the entire shaft 102 as well as rotation of the handle 120. Clearly, the device 100 provides the medical practitioner with the ability to reposition the distal end 112 using a single hand.

Figure 5B:
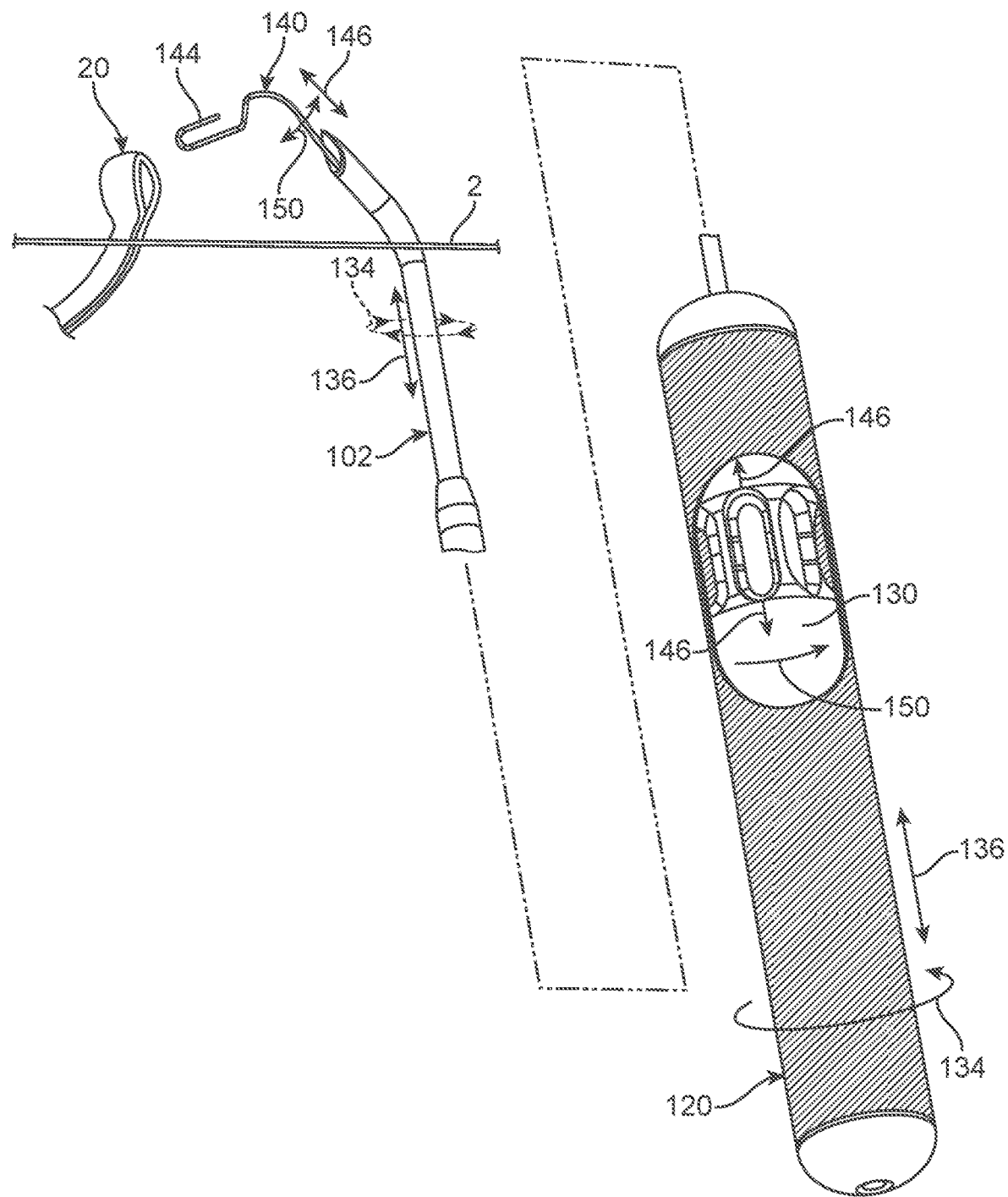

FIG. 5B illustrates a configuration where the carrying element 140 advances in an axial direction 146 upon a corresponding axial movement 146 of the actuator 130 coupled to the handle 120. As noted above, some variations of the instrument 100 allow for simultaneous rotation 150 of the actuator, which produces corresponding rotation 150 of the carrying element 140. In addition, the handle 120 can be rotated 134 and/or axially moved 136 to produce corresponding rotation 134 and/or axial movement 136 of the shaft 102. In those procedures where the instrument 100 is used to retrieve a suture 120, the manipulation of the handle 120 and actuator 130 are used to position the capturing element 144 adjacent to the suture 20.

Figure 5C:
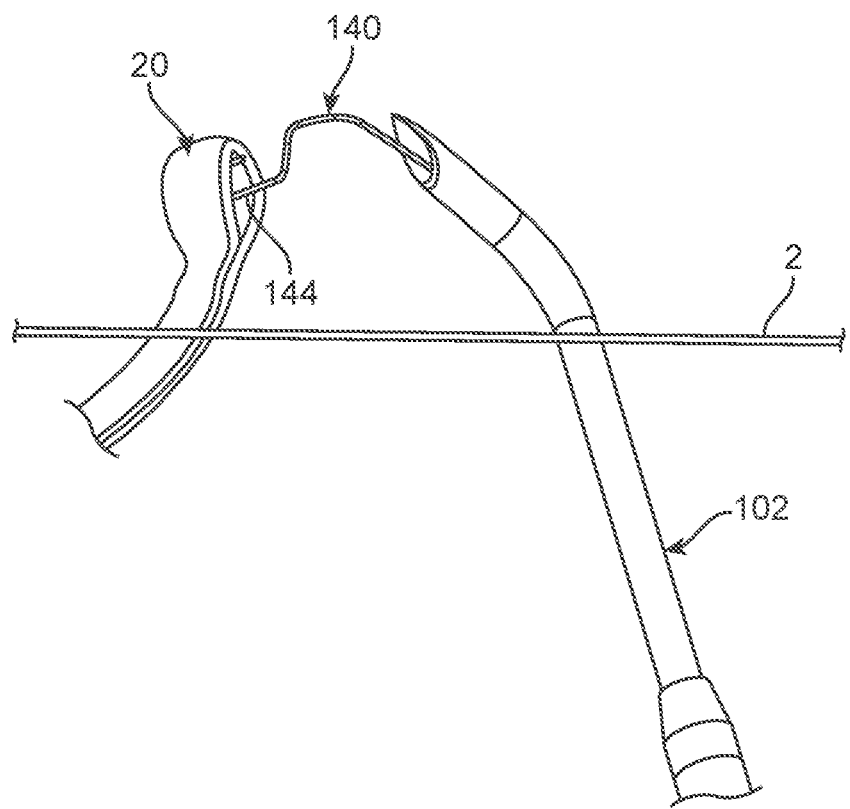
Figure 5D:
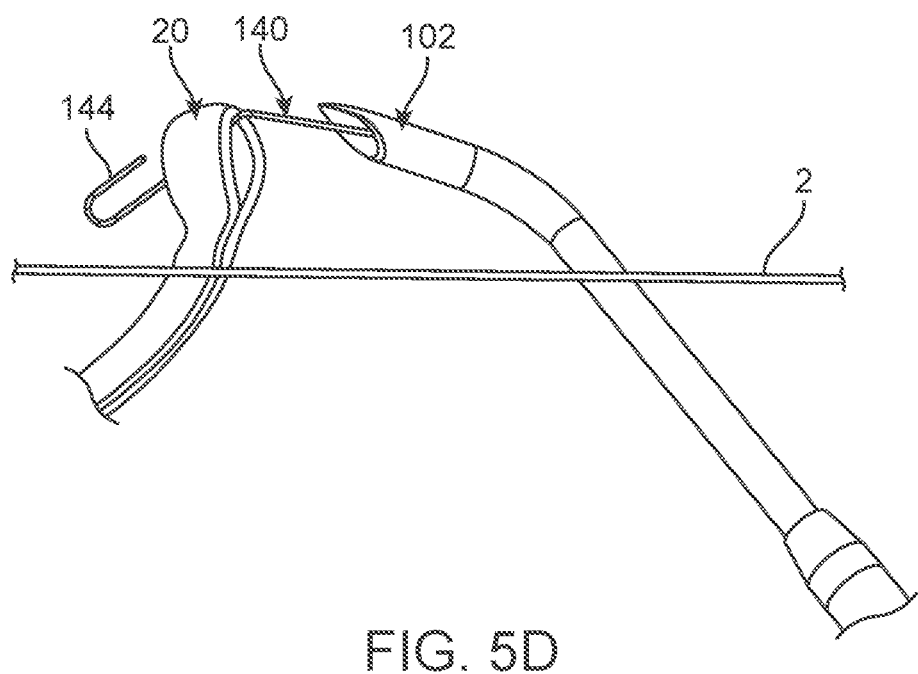

FIG. 5C illustrates the carrying element 140 as being advanced into a loop of the suture 20. As noted above, in alternate variations the suture 20 will include a knot, needle, hook, etc. that is used to engage the capture portion 144. FIG. 5D shows the capture portion 144 of the carrying element 140 advancing beyond the suture 20. As noted herein, the capturing portion 144 as well as the remaining portion of the carrying element 140 can be fabricated to be elastically deformable to assist in navigating to and securing the suture 20.

Figure 5E:
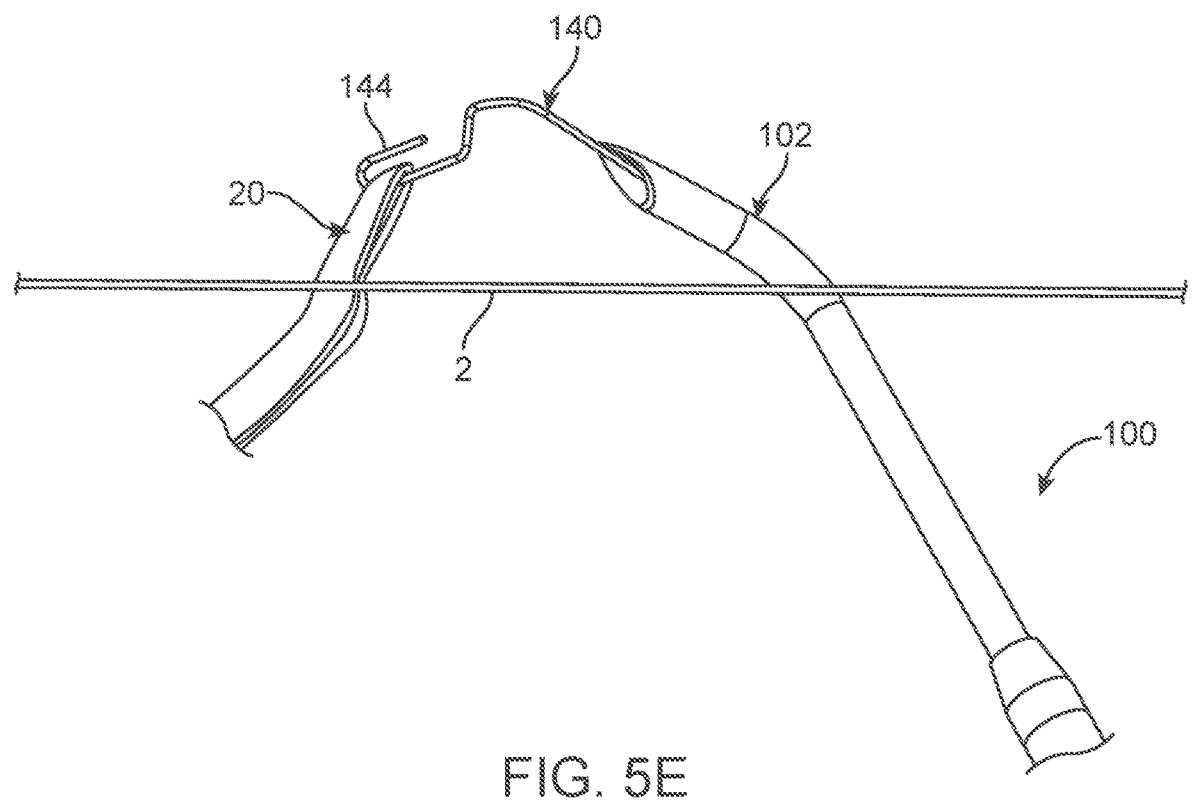
Figure 5F:
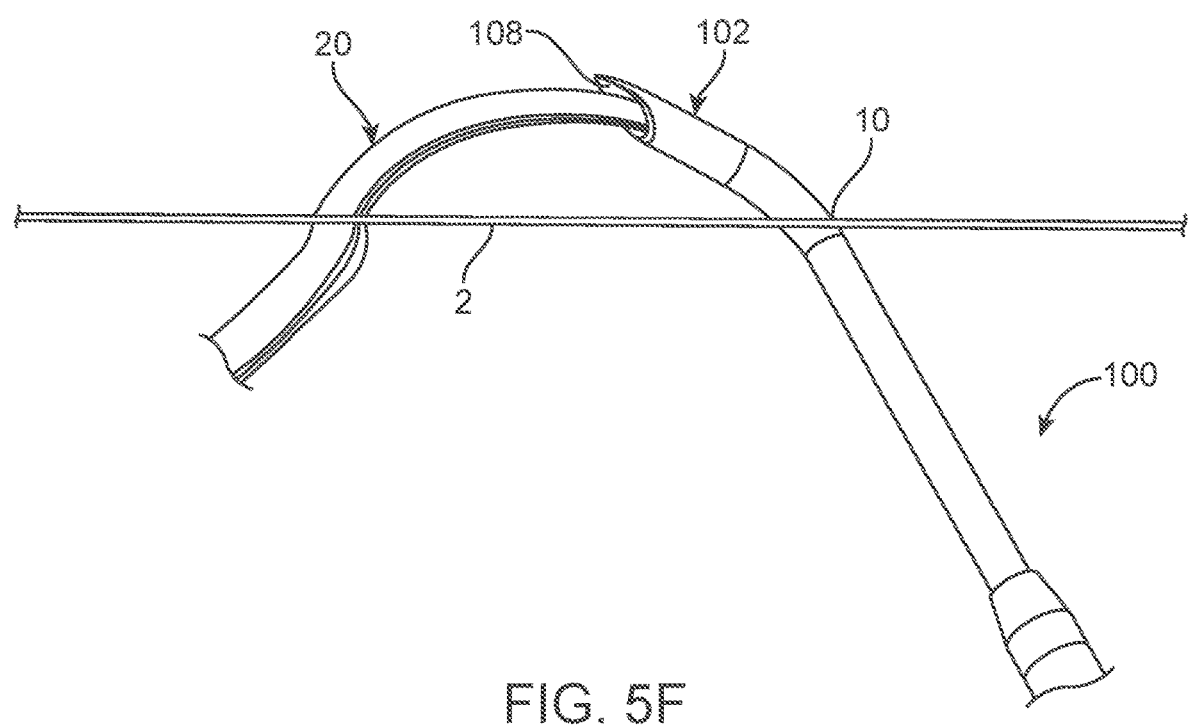

FIG. 5E illustrates the situation where either the device 100 and/or the carrying element 140 is withdrawn relative to the suture 20 to secure the suture 20 within the capturing portion 144. FIG. 5F shows further withdrawal of the carrying element (not illustrated in FIG. 5F) into the opening 108 of the shaft 102 to partially draw the suture 20 within the shaft 10 such that retrieval of the device 100 causes the suture 20 to be pulled through the shaft opening 10 and through the tissue 2.

Although not illustrated, a suture 20 can be initially advanced through the tissue 2 using an instrument (i.e., a placement instrument). In such a situation, the suture can either extend outside of the placement instrument or extend within a shaft of the placement instrument. A second device (i.e., a retrieval instrument) can be used to secure a portion of the suture thereto. This allows the retrieval instrument to be withdrawn back through tissue. A benefit of this dual instrument procedure is that both devices can be manipulated using either hand of the medical practitioner.

Figure 6A:
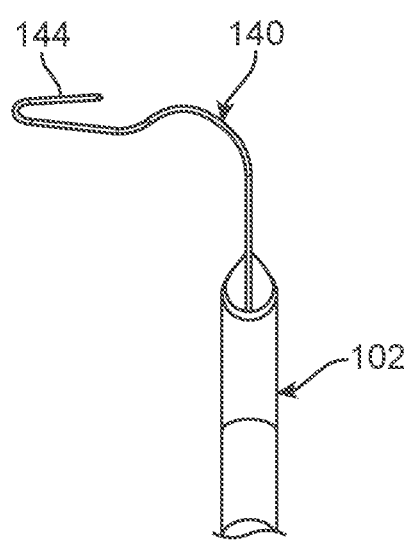
FIGS. 6A to 6D illustrate some additional variations of carrying elements with various types of capturing portions at an end of the shaft.
Figure 6B:
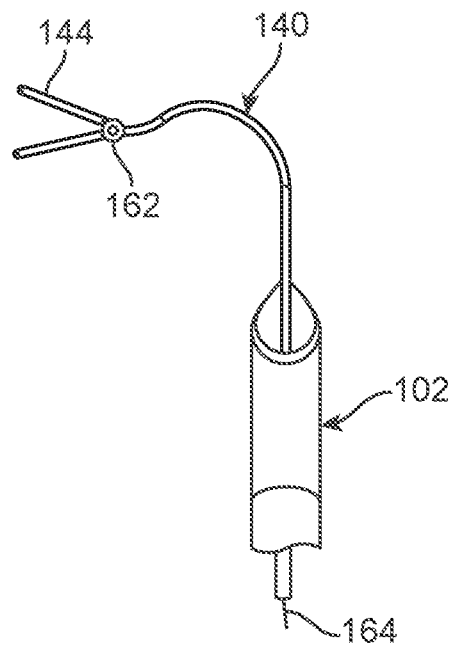
Figure 6C:
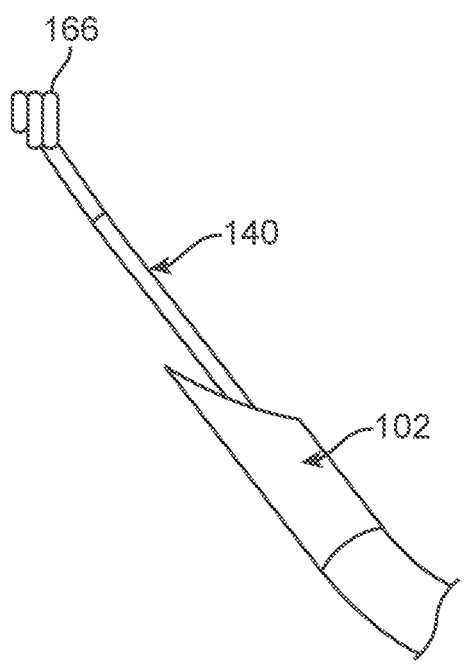
Figure 6D:
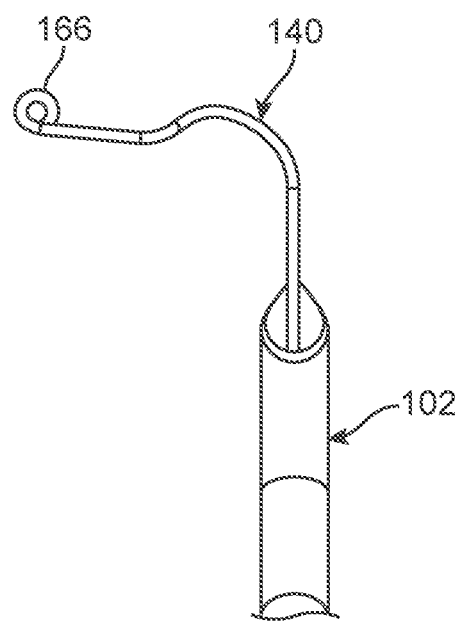

FIGS. 6A to 6D illustrate some additional variations of carrying elements 140 with various types of capturing portions 144 at an end of the shaft 102. FIG. 6A illustrates a capture portion 144 that has a v-shape where the open legs of the v-shape are proximal to an apex of the v-shape. FIG. 6B illustrates an actuatable capture portion 155 having a jaw structure joined at a hinge 162. The jaw structure can be operated using one or more pull wires 164 that extends to a proximal end of the device and/or to a handle of the device. FIGS. 6C and 6D illustrate a carrying element 150 having a capturing portion configured in a coil structure 166. In such a case, the coil 166 can be flexible such that a suture becomes secured within the turns of the coil 166. Although not illustrated, the turns of the coil 166 can be in contact or can be separated by a gap.

Figure 7A:
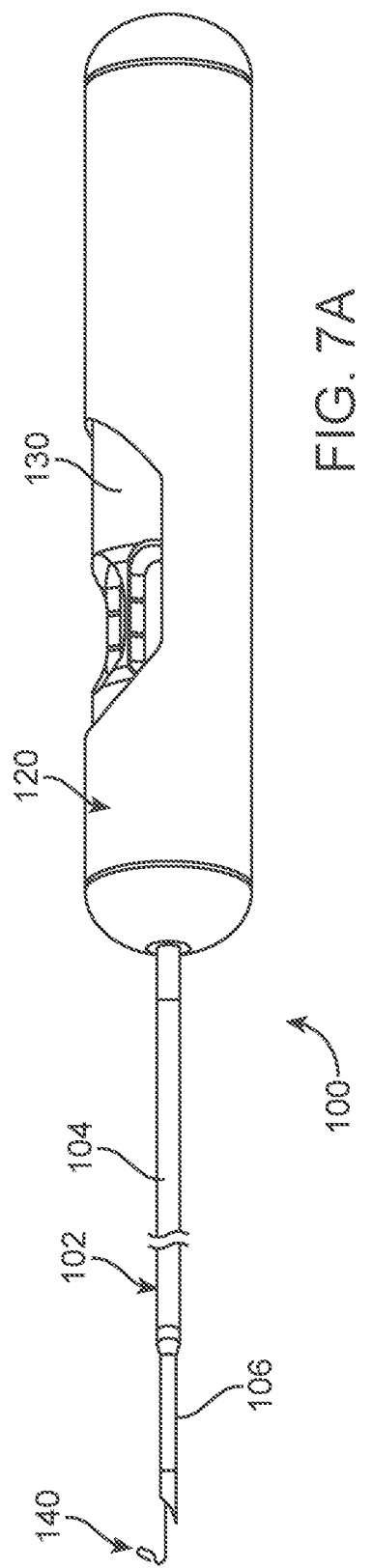
FIGS. 7A and 7B show alternative shaft configurations of variations of the instrument described herein.
Figure 7B:
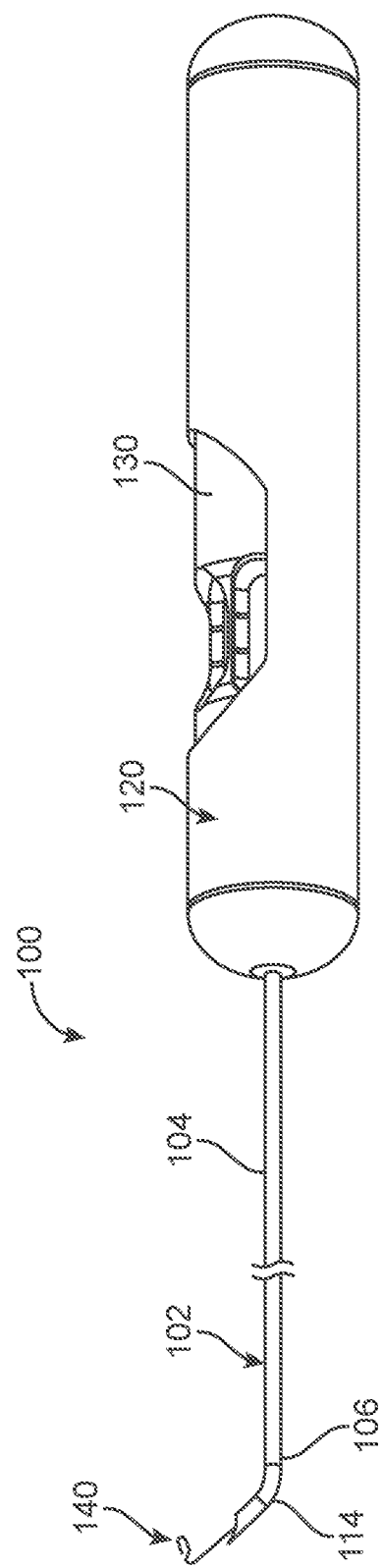

FIGS. 7A and 7B illustrate additional variations of devices 100 as described herein. For example, FIG. 7A illustrates an actuator 130 within a handle 120, where the handle 120 is coupled to a shaft 102 where the far portion 106 of the shaft 102 is straight. FIG. 6B illustrates a shaft 102 coupled to a handle 120 where the near portion 104 and far portion 106 of the shaft are the same or similar diameters (e.g., the shaft 102 can comprise a single tubular member).

Figure 8:
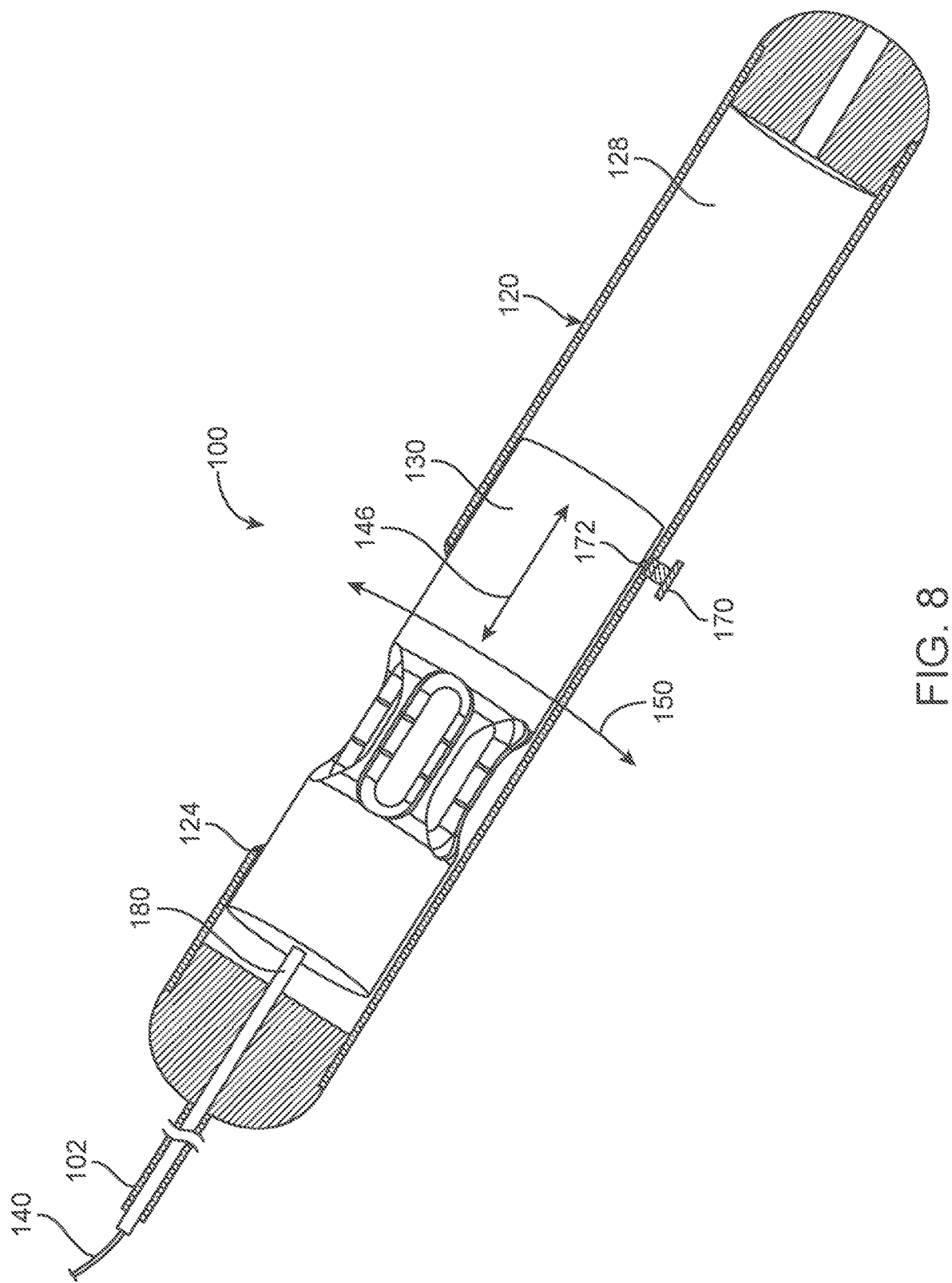
FIG. 8 illustrates a cross sectional view of a handle with a cylindrical actuator floating within the actuator.

FIG. 8 illustrates another aspect of variations of devices 100 under the present disclosure. As shown, another feature of the device 100 is that the handle body 120 comprises a bore 128 that accommodates a free-floating sliding fit with an actuator 130. Although the actuator 130 is shown to be a substantially solid cylindrical piece, it can comprise any structure that has an effective cylindrical profile such as a varying surface comprising peaks and grooves where the peaks effectively form a cylindrical circumference that forms a sliding fit with the bore 128 of the handle 120. Moreover, variations of the device 100 include a body 120 that is non-cylindrical on an outer surface but comprises a bore 128 that is sized to allow a sliding fit with the actuator 130. In the illustrated variation, the body 120 comprises a cylindrical surface, which allows for a medical practitioner to grasp the body 100 with a palm of their hand and use their fingers to aid in manipulation of the body 100 while the thumb can be used to provide axial movement 146 of the actuator and/or rotational movement 150 of the actuator to drive a torque shaft 180 relative to a shaft 102 that is affixed to the body 120. Such a handle configuration can be used for the carrying element 140 as described herein. Moreover, this handle configuration can be used in a number of other medical devices used in arthroscopic, thorascopic, and/or endoscopic procedures.

FIG. 8 also shows the device 100 as having a tensioning component 170 having a tensioning surface 172 that can adjust a force required to move the actuator 130 within the bore 128. For example, the tensioning component 170 and surface 172 can comprise a spring loaded ball-bearing that applies an adjustable force on a portion of the handle 130.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described. For example, the invention includes combinations of aspects of the variations of the devices described herein as well as the combination of the variations themselves. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

We claim:

1. A surgical instrument for manipulating a suture, the surgical instrument comprising:
   a shaft having a far portion and a near portion;
   a lumen extending through the shaft to an opening at the far portion;
   a handle at the near portion of the shaft;
   a suture carrying element comprising a main segment having an arcuate element segment and a capture portion at a distal end, the capture portion having a first leg adjacent to the arcuate element segment, a seat connecting the first leg to a second leg, the seat having an arc shape such that the second leg extends back towards the arcuate element segment, where a free end of the second leg is opposite to the seat and forms an opening between the first leg and the second leg that opens towards the arcuate element segment, the opening configured to receive the suture;
   wherein when the arcuate element segment is advanced out of the shaft the capture portion extends radially away from an axis of the main segment, the suture carrying element being elastically deformable when withdrawn within the lumen, and movement of the arcuate element segment within the opening deforms the arcuate element segment causing movement of the capture portion through an arc profile independently of the shaft, where a shape of the capture portion does not change during movement through the arc profile; and
   an actuator housed in the handle and coupled to the main segment of the suture carrying element, the actuator being moveable relative to an axis of the handle in a rotational direction and in an axial direction, such that the suture carrying element can rotate and advance either independently or simultaneously relative to the shaft with movement of the actuator.

2. The surgical instrument of claim 1, further comprising an arcuate shaft segment located between the far portion and the near portion such that a far end of the shaft extends radially away from an axis of the near portion.

3. The surgical instrument of claim 1, where the shaft is fixed relative to the handle such that rotation of the handle causes rotation of the shaft.

4. The surgical instrument of claim 1, wherein the arcuate element segment comprises an arc angle greater than ninety degrees.

5. The surgical instrument of claim 4, wherein the arcuate element segment is configured to cause the capture portion to re-enter the opening at the far portion in a single position relative to the opening.

6. The surgical instrument of claim 1, wherein the actuator is positioned within the handle and is moveable relative to the axis of the handle simultaneously in the rotational direction and in the axial direction while the handle remains stationary.

7. The surgical instrument of claim 1, further comprising a torque shaft extending in the lumen and coupling the main segment to the actuator, wherein a torsional stiffness of the torque shaft is greater than a torsional stiffness of the main segment such that the torque shaft transfers rotation to the main segment.

8. The surgical instrument of claim 7, wherein the torque shaft comprises a stainless-steel hypodermic tubing.

9. The surgical instrument of claim 7, where an arc of the arcuate element segment is greater than ninety degrees such an apex of the arcuate element segment is positioned distally of the first leg, such that when a suture is located against the apex, distal movement of the suture capturing element urges the suture towards the seat.

10. The surgical instrument of claim 1, wherein the seat forms a u-shaped profile.

11. The surgical instrument of claim 7 further comprising a reinforcement member coupled to a portion of the main segment to form a reinforced segment, such a torsional stiffness of the reinforced segment is greater than a torsional stiffness of a remainder of the main segment such that the torque shaft transfers rotation to the remainder of the main segment.

12. The surgical instrument of claim 1, where the shaft is rigid.

13. The surgical instrument of claim 1, where the shaft is malleable.

14. The surgical instrument of claim 1, where the capture portion is angled forty-five degrees relative to an axis of the main segment.

15. The surgical instrument of claim 1, further comprising a sharp tip located at a far end of the far portion, which allows the far end of the shaft to penetrate through soft tissue when advanced therethrough.

16. The surgical instrument of claim 1, where the handle further comprises a window opening and where the actuator is accessible through the window opening.

17. The surgical instrument of claim 16, where the actuator is recessed within the window opening.

18. The surgical instrument of claim 1, where the suture carrying element comprises a superelastic alloy.

19. The surgical instrument of claim 1, wherein the capture portion comprises an opening disposed proximal to the distal end including a distal concave surface facing proximally for retaining the suture within the opening as the surgical instrument is drawn proximally.

20. The surgical instrument of claim 1, wherein the capture portion comprises a v-shape wherein the seat is formed by an apex of the v-shape, where the apex is distal to the opening.

21. A method for manipulating a suture passed through a tissue, the method comprising:
   positioning a shaft adjacent to the tissue using a handle, the shaft having a sharp distal tip;
   passing a distal opening of the shaft through the tissue and advancing the shaft through the tissue;
   manipulating an actuator in the handle to advance a suture carrying element through a lumen of the shaft, where the suture carrying element comprising a main segment having an arcuate element segment and a capture portion at a distal end, the capture portion having a first leg adjacent to the arcuate element segment, a seat connecting the first leg to a second leg, the seat having an arc shape such that the second leg extends back towards the arcuate element segment when the suture carrying element is unconstrained, where a free end of the second leg is opposite to the seat and forms an opening between the first leg and the second leg that opens towards the arcuate element segment;

rotating the suture carrying element relative to the shaft while moving the actuator to engage a portion of the suture within the opening remotely from the shaft and without deforming the capture portion;

retracting the capture portion towards the shaft, where movement of the arcuate element segment in the distal opening deforms the arcuate element segment to cause the capture portion to move in an arc profile while the arcuate element segment moves within the distal opening;

positioning the capture portion and the suture within the shaft; and withdrawing the shaft through the tissue to pull the suture through the tissue region.

22. The method of claim 21, where the arcuate element segment comprises an arc angle greater than ninety degrees, such that such an apex of the arcuate element segment is positioned distally of the first leg, the method further comprising distally advancing the apex against the suture to urge the suture into the u capture portion.

\* \* \* \* \*